United States Patent
Crosato

(10) Patent No.: US 9,260,681 B2
(45) Date of Patent: Feb. 16, 2016

(54) FERMENTATION APPARATUS

(75) Inventor: Remo Crosato, San Biagio di Callalta (IT)

(73) Assignee: L.A.S.I. S.R.L., Meolo (Venezia) (IT)

(*) Notice: Subject to any disclaimer, the term of this patent is extended or adjusted under 35 U.S.C. 154(b) by 926 days.

(21) Appl. No.: 13/255,763

(22) PCT Filed: Mar. 18, 2009

(86) PCT No.: PCT/EP2009/053191
§ 371 (c)(1),
(2), (4) Date: Sep. 9, 2011

(87) PCT Pub. No.: WO2010/105676
PCT Pub. Date: Sep. 23, 2010

(65) Prior Publication Data
US 2011/0318823 A1    Dec. 29, 2011

(51) Int. Cl.
| | | |
|---|---|---|
| *C12G 1/02* | (2006.01) | |
| *C12F 3/02* | (2006.01) | |
| *C12M 1/107* | (2006.01) | |
| *C12M 1/02* | (2006.01) | |
| *C12M 1/00* | (2006.01) | |

(52) U.S. Cl.
CPC ... *C12G 1/02* (2013.01); *C12F 3/02* (2013.01); *C12M 23/36* (2013.01); *C12M 27/00* (2013.01); *C12M 29/24* (2013.01)

(58) Field of Classification Search
CPC ............ C12F 3/02; C12G 1/02; C12M 29/24; C12M 27/00; C12M 23/36
See application file for complete search history.

(56) References Cited

U.S. PATENT DOCUMENTS 3,959,120 A * 5/1976 Pollock et al. ............. 435/294.1
4,021,579 A    5/1977 Barrett

FOREIGN PATENT DOCUMENTS

| AT | 005698 U1 | 10/2002 | |
|---|---|---|---|
| EP | 0530820 A2 | 3/1993 | |
| EP | 1314778 A1 | 5/2003 | |
| EP | 1616937 A1 | 1/2006 | |
| EP | 1 964 914 | * 3/2009 | ............... C12G 1/02 |
| EP | 2058384 A1 | 5/2009 | |
| WO | WO 98/45403 A1 | 10/1998 | |
| WO | WO 2005/023977 A1 | 3/2005 | |
| WO | WO 2006/087601 A1 | 8/2006 | |

* cited by examiner

*Primary Examiner* — Gautam Prakash
(74) *Attorney, Agent, or Firm* — Birch, Stewart, Kolasch & Birch, LLP

(57) ABSTRACT

An apparatus for the fermentation of a vegetable product in the form of crushed material, includes a first tank for containing the crushed material and a second collection tank for the gaseous products generated from the crushed material's fermentation, a first piping system adapted to let communicate a part of the first tank, where the gaseous products are gathered, with the second tank, a second piping system adapted to let communicate the second and the first tank, the system having a outlet in the first tank where, in use, the liquid of the crushed material is present, first and second valves associated respectively to the first and second piping system to make the two tanks selectively communicating conditionally to the open/closed status of said valves. To allow fermentation in controlled environment there are provided an adjustment device adapted to finely adjust the gaseous product's pressure to one or more values programmed by a user inside the first and second tank when they are communicating and/or within the second tank when it is isolated.

8 Claims, 2 Drawing Sheets

FERMENTATION APPARATUS

BACKGROUND OF THE INVENTION

1. Field of the Invention

The invention relates to a fermentation apparatus.

Although the invention is useful for the fermentation of any vegetable product in the form of a crushed material, the description that follows will refer as an example to winemaking, where the invention has proved particularly effective.

2. Description of Background Art

Winemaking is carried out with the help of special tanks, where the must is introduced to ferment. The fermentation process generates large amounts of gaseous products, especially $CO_2$, participating actively to the success of a good wine. The gases are released from the must and push the marc and every solid part upward where they compact and form a solid layer, called "cap".

The winemaking methods exploit the fermentation gases, as in WO 98/45403, to mix the cap and prevent solidification thereof. In combination or not, other methods consider to adjust the pressure inside the winemaking tank through safety or degassing valves, both mechanical or membrane valves.

An example of pressure adjustment is described in WO 2006/087601. Here a particular type of degassing valve is used, of the membrane type, in which fluid is pumped to tighten it and lock the vent thereof.

Recently, the applicant has surprisingly discovered how much the pressure inside the winemaking tank is very important, especially during the degassing. Too high a pressure in the tank has immediate repercussions on the quality of wine. The degassing, impulsive or not, induce the must to surface on the cap and the release of gases from within the grape berries. If the pressure is too high, the berries brake and a lot of dregs (mush suspended in the must) is produced. It has been discovered that each grape has its optimum fermentation pressure, which must be regulated with a maximum tolerance of one hundredth of bar (e.g. values as precise as 0.29 bar or 0.31 bar).

The membranes in WO 2006/087601 are made of rubber or similar, and suffer greatly from many factors such as their inertia, whereby they regulate very approximately their venting, or the temperature. A pressure maintained at 0.3 bar during the day can move also to 0.2 bar at night, when the cellar is colder. Moreover, the more the internal pressure of the tank is approaching the threshold pressure, the more sensitivity and precision is lost in the valve, because the membranes are beginning to open. Swinging values with errors of 0.1 bar in WO 2006/087601, which is about 25% of the usual maximum working pressure, are not adequate for a controlled-pressure fermentation. Not only can the must be denatured, but also could the proper fermentation process of grapes be altered through wrong pressures. The same goes for mechanical valves with spring pressure adjustment and calibration.

SUMMARY OF THE INVENTION

This and known winemaking apparatuses can be improved, and such is the object of the present invention, which wants to present an apparatus for the fermentation of a vegetable product in the form of crushed material, preferentially must, which allows to establish inside a fermentation (e.g. vinification) tank a pressure of the gases produced by fermentation with very precise value.

Another object is to enable the setting of programmed pressure trends inside the (e.g. vinification) tank.

This object is achieved with an apparatus for the fermentation of a vegetable product in the form of crushed material, preferentially must, comprising a first tank for containing the crushed material and a second collection tank for the gaseous products generated from the crushed material's fermentation, a first piping system adapted to let communicate a part of the first tank, where the gaseous products are gathered, with the second tank, a second piping system adapted to let communicate the second and the first tank, the system having an outlet in the first tank where, in use, the liquid of the crushed material is present, first and second valve means associated respectively to the first and second piping system to make the two tanks selectively communicating conditionally to the open/closed status of said means; characterized by comprising adjustment means adapted to finely adjust the gaseous products pressure inside at least one tank at one or more values programmed by a user.

With the invention the pressure inside either, or both, tanks can be adjusted very finely (with error about the hundredth of bar). In the standard pressure range used (0.15-0.5 bar) an enologist or generally a user can customize the value and/or trend of pressure over time, for example in a pump-over cycle and/or on different cycles in sequence.

All this provides the wine specialist enormous potential for winemaking. As mentioned above the pressure in the vinification tank affects a lot the quality and type of wine produced. Variables such as the type of grape, vintage, temperature and the degree or stage of fermentation combine with the pressure variable in a single recipe to give the final wine.

In addition, the apparatus of the invention better adapts to receive more types of grapes, because it can process them creating a fermentation environment precisely pressure-controlled. For each grape specific parameters of pressure are needed, although very different from grape to grape; with the invention, the winemaking apparatus is able to offer an optimal and adaptable environment for vinification.

Thus, it is preferred that the adjustment means are adapted to adjust the gaseous products pressure with an error less than or equal to 0.01 bar.

To achieve such great precision, preferably the adjustment means comprise valve means, a processing unit, a pressure sensor for detecting the inner pressure of the tank to be stabilized, the unit being adapted to read the data outputted by the sensor and adjust the third valve means so as to maintain the pressure on a programmed value. In practice, a feedback control is carried out.

As valve means one may use:

a single valve, mounted between the first tank and the outside, or a single valve, mounted on the first piping system between the first valve means and the second tank;

two valves, one rough and one more precise in parallel, placed on the first tank or the first piping system.

Preferably the valves are of the open/close type, so that the processing unit can constantly open and close the additional valve(s) to vent little excess gas at a time with respect to the programmed pressure.

Much depends on the volume of gas to degas. For a very large tank, there may be a sole valve and also of not refined mechanics, because the inaccuracy about its vent flow becomes negligible compared to a much larger volume of gas. Conversely, for smaller tanks there is needed a valve with precise and controlled vent, so for example in parallel to a safety valve, used for violent instantaneous degassing, a small electromechanical open/close valve may be placed. The whole meets the specific demands of accuracy.

However, a slower degassing can always happen with a single pressure finely-regulating valve.

BRIEF DESCRIPTION OF THE DRAWINGS

To make clear the benefits of the invention, a preferred apparatus will now be described according to the invention with reference to the drawings, where.

DETAILED DESCRIPTION OF THE INVENTION

Figure 1:
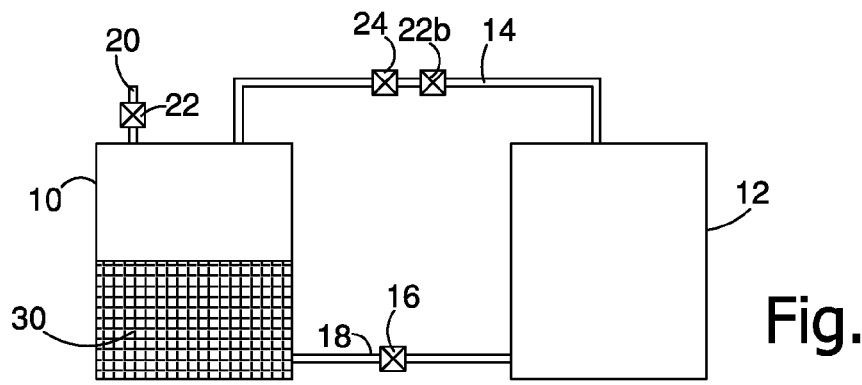
FIGS. 1-4 show a winemaking apparatus according to the invention in various steps of operation.

A tank 10 (FIG. 1) is filled by known means and ways with must 30. A conduit 14 puts in communication in a controllable manner, through a valve 24, the upper part of the tank 10 with the upper part of a second tank 12. A second conduit 18 puts into communication in a controllable manner, through a valve 16, the bottom of the tank 10 with the bottom of the tank 12. The tank 10 has an upper vent 20 controllable by pressure adjusting means 22. The valve 16 is initially closed to block a reflux of the must 30.

Figure 2:
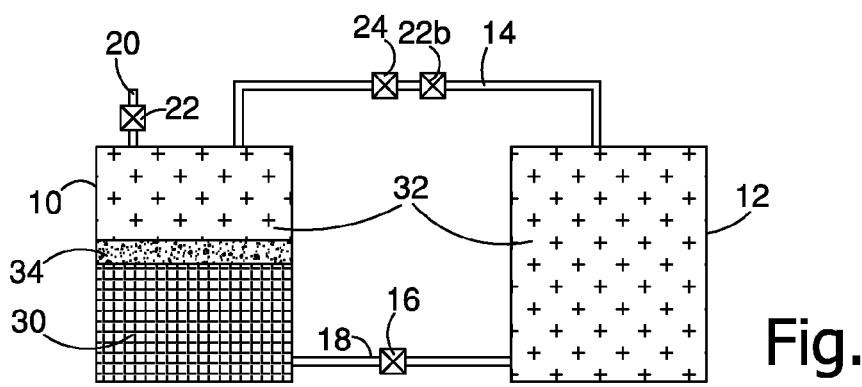

After a certain time (FIG. 2) the must 30 generates fermenting a gas or gaseous products 32 (mainly $CO_2$) and creates a solid cap 34. The valve 24 is open and spontaneously the gas 32 invades the tank 12. The pressure adjusting means 22 are regulated to prevent the escape of the gas 32 from the tank 10.

Figure 3:
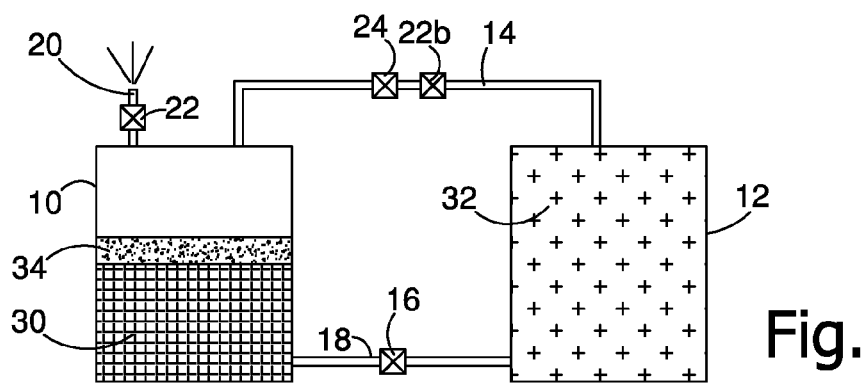

After a predetermined time, the tanks 10, 12 are isolated by closing the valve 24. The gas 32 gets trapped in pressure in the tank 12, while the other is depressurized (or degassed) through the conduit 20 by adjusting the pressure adjusting means 22 so as to open the conduit 20 (FIG. 3).

Figure 4:
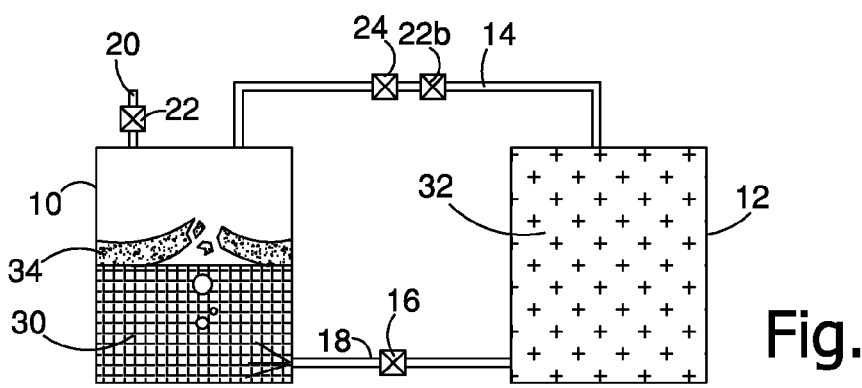

Finally, (FIG. 4), the valve 16 opens and the gas 32 flows spontaneously in the must 30. While going up it will determine the soft rupture of the cap 34 and its leaching, thereby extracting the natural flavorings and colorings therefrom.

The pressure adjusting means 22 are controlled by an electronic unit (not shown), e.g. a PLC, which manages all the steps of winemaking. This unit may implement programming user interfaces and driving stages for the pressure adjusting means 22. Through control of the means 22, the unit can accurately maintain any particular planned pressure inside the tank 10. To this aim, the unit is interfaced with a pressure sensor (not shown) which measures the gas pressure in the tank 10.

As a pressure adjusting means one can use valve means, for example a single valve, mounted between the first tank 10 and the external environment or two, one rough and one more precise in parallel. Preferably the valves are of the open/close type, so that the processing unit can constantly open and close the additional valve(s) to vent a little gas at a time.

The pressure inside the gas accumulation tank 12 is very important. In fact, too high a pressure in this tank has a huge influence on wine quality. The release, impulsive or not, of the gas 32 stored under pressure from the tank 12 to tank 10 (and below the marc cap), induces a more or less violent break of the marc cap, the surfacing of must on the cap and the release of gas from the inside of grape berries. If the pressure is too high, the berries brake and a lot of dregs is produced (mush suspended in the must).

It has been discovered that each and every grape and marc cap (in connection both to vintage, and to the harvest time of grapes and even the same manner in which the grapes are collected, e.g. by mechanical or manual harvesting) has its optimum pressure for the pump-over gas, which must be regulated with a maximum tolerance of one hundredth of bar (e.g. as precise a value as 0.29 bar or 0.31 bar).

It may be understood how the invention ensures even in this case the optimal fermentation environment for the must.

In FIGS. 1-4 is shown another valve 22b, optional or in replacement to the valve 22, placed on the conduit 14 with the vent directed to the outside. In particular, when the valve 22b is present, the apparatus allows more control to be performed over winemaking. Consider, for example, the case wherein the valve 22 is absent (reduced number of components).

The gas storage in the tank 12, with the valve 24 open, occurs as stated above, but the valve 22b allows in this step to control the pressure of gas 32 in the tank 10, i.e. there is the control of the pressure which the must 30 and the cap 34 experience during fermentation.

With the valve 24 closed the gas 32 gets trapped in the tank 12, as already mentioned, but the valve 22b now allows when necessary to control the pressure in the tank 12. This allows to adjust the pressure of the gas 32 which knocks the must 30 and the cap 34 in the next step of pumping-over.

It is clear how in this case the invention with only two vent valves ensures absolute control of all the crucial pressures in the winemaking apparatus.

Figure 5:
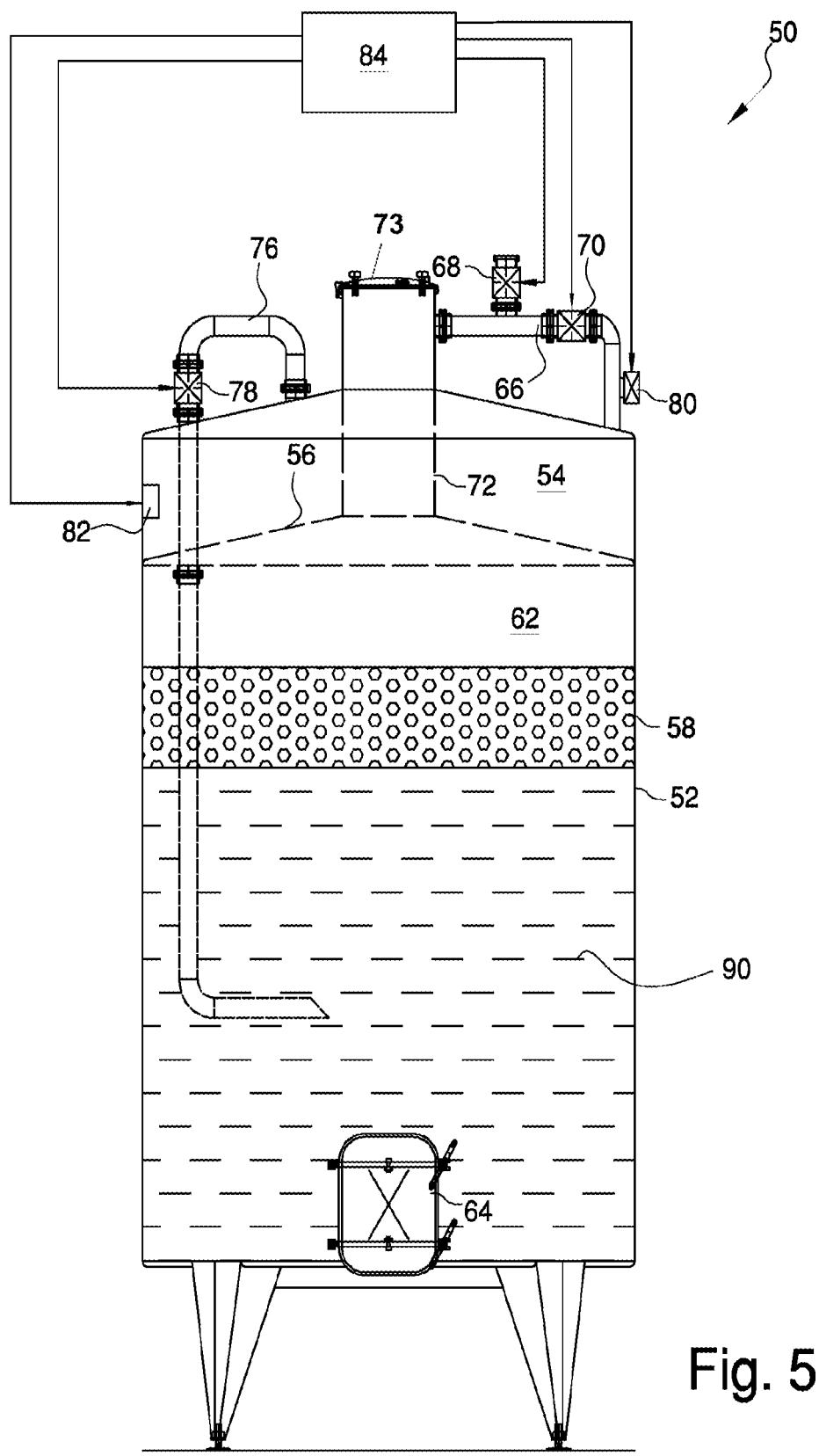
FIG. 5 shows another preferred form of the winemaking apparatus according to the invention, denoted by 50.

For a more compact version and with two valves see FIG. 5. A winemaking apparatus 50 for some must 90 consists of a cylindrical casing 52 internally divided by a conical-cap separating wall 56 in two stacked sub-tanks 54, 62, upper and lower respectively.

The volume 62 communicates with the outside through a base hatch 64 and a vertical hatch 72, around which the tank 54 develops.

The upper tank 54 is selectively connectable to the hatch 72 via a conduit 66 and a valve 70. On the same conduit 66 there is a second valve 68 with the function of making communicating the hatch 72 (and thus the tank 62) with the outside world for the degassing (when its closing door 73 is closed). On the conduit 66, between the valve 70 and the tank 54, is mounted another valve 80 of the electromechanical open/close type, smaller than the valve 68, and therefore more sensitive and with limited flow. Its goal is to finely adjust the pressure inside the tanks 62, 54.

The tank 54 is also selectively connectable to the tank 62 via a conduit 76 and a valve 78.

The valves 70, 68, 78, 80 are controlled by an electronic unit 84, for example a PLC, which manages all the steps of winemaking. This unit 84 may implement timers, programming user interfaces and driving stages for the valves 68, 70, 78, 80 (see arrows in FIG. 5).

Through the control of the valve 80, specially designed to release a small amount of gas at a time to the outside (i.e. it has a very small controllable flow so as to regulate the hundredth of bar in the tank 62 and/or 54), the unit 84 can maintain precisely any particular planned pressure inside the tank 62 and/or 54. For this aim, the unit 84 is interfaced with a pressure sensor 82, which measures the gas pressure in the tank 54.

The operation of the winemaking apparatus 50 is the same as described for FIGS. 1-4, being enough to keep in mind the following correspondence:

tank 10 ↔ tank 62
tank 12 ↔ tank 54
valve 22 ↔ valve 68
valve 24 ↔ valve 70
valve 16 ↔ valve 78
conduit 14 ↔ conduit 66 conduit 18↔ conduit 76 valve 22b↔ valve 80.

The overall operation will be repeated succinctly for the main steps.

Basically, the proper driving of the valves 70, 68, 78 allows to accumulate in the tank 54 the gaseous products of fermentation in order then to discharge them into the tank 62 to break a marc cap 58.

(i) The tank 62 is filled with must 90.

(ii) After some time the fermenting must 90 generates some gas and a solid cap 58. The valve 70 is open, the valve 68 and the valve 78 are closed. Therefore spontaneously the gas invades tank 54. The valve 80 will be adjusted, for example with cycles having proper duty-cycle of short opening alternated to closure, so as to maintain the two tanks 54, 62 at a predetermined pressure, defined by the user by programming the unit 84. Such pressure can be either constant or follow a programmed reference trend, and corresponds to the pressure which the must 90 and the cap 58 undergo.

(iii) After a scheduled time, the valve 70 is closed. The gas remains trapped in pressure in the tank 54, while the other tank 62 is depressurized (or degassed) by opening the valve 68, which is designed to withstand even a violent outflow. Now with the valve 80 the pressure in the tank 54 can be adjusted to a value even different from the previous one (by also introducing, or not, into the tank 54 compressed air or other process-compatible gases).

(iv) the valve 78 is opened and the gas flows spontaneously into the must 30 and while going up it interacts with the cap 58, breaking it. Because the gas pressure was adjusted to a precise value, which is the optimal one for the processed grapes, the interaction with the must and the cap is the best possible.

It is clear that every phase (i-iv) can be advantageously automated and/or programmed by the unit 84. This allows to set cycles, periodic or not, of breaking the cap 58, and to test various methods of degassing the tank 62. In particular the best value, and/or that trend, for the pressure in the tanks 54, 62 (values and trends also being independent between each other) can be found, which gives optimal results for the wine. The same applies to the apparatus of FIG. 1.

The invention claimed is:

1. Apparatus for the fermentation of a vegetable product in the form of crushed material, comprising:
    a first tank for containing the crushed material and a second collection tank for the gaseous products generated from, fermentation of the crushed material;
    a first piping system adapted to allow communication of a part of the first tank, where the gaseous products are gathered, with the second tank;
    a second piping system adapted to allow communication of the second tank and the first tank, the second piping system having an outlet in the first tank where, in use, the liquid of the crushed material is present;
    a first valve and a second valve associated respectively to the first piping system and the second piping system to make the first and second tanks selectively communicating conditionally to the open/closed status of said first and second valves, so that:
        by opening the first value and closing the second valve, the gaseous product invades under pressure the second tank; and
        only the gas stored in the second tank can be released inside the first tank when the second valve is opened and the first valve is closed;
    a third valve;
    a fourth valve connected in parallel with the third valve;
    a processor; and
    a pressure sensor configured to detect the inner pressure of the tank to be stabilized, wherein the tank to be stabilized is either the first tank or the second tank, or both the first tank and the second tank,
    wherein the third valve is mounted and configured to vent the first tank towards the outside and destined to instantly degas the first tank towards the outside, and the fourth valve is configured to adjust the pressure of the tank to be stabilized,
    wherein the fourth valve is further configured to adjust the pressure of the gaseous product, with an error less than or equal to 0.01 bar, and
    wherein the processor is configured to read the data outputted by the sensor and adjust the third and fourth valves so as to maintain the pressure on a programmed value, programmed by a user, inside the first and second tanks when the first and second tanks are communicating, or inside the second tank when the second tank is isolated.

2. Apparatus according to claim 1, wherein the third valve is mounted on the first piping system between the first valve and the second tank.

3. Apparatus according to claim 1, wherein the third valve is of the open/close type.

4. Apparatus according to claim 1, wherein the pressure sensor is mounted to monitor the pressure in the second tank.

5. Apparatus according to claim 1, wherein the processor is provided with a memory and is programmed to adjust, through driving of the fourth valve, the pressure in the first tank so that it follows a programmed reference trend stored in the memory.

6. Apparatus according to claim 1, comprising an outer casing divided internally by at least one separating wall in two sub-volumes which form the first and the second tank.

7. Apparatus according to claim 6, wherein said first and second tanks are arranged vertically one over the other inside the casing.

8. Apparatus according to claim 6, wherein said first and second tanks are two physically independent tanks connected together through a first and a second piping system.

* * * * *